US00PP19608P2

(12) United States Plant Patent
Cannon

(10) Patent No.: US PP19,608 P2
(45) Date of Patent: Dec. 30, 2008

(54) SOUTHERN LIVE OAK TREE NAMED 'CANNON-SHARP'

(50) Latin Name: *Quercus virginiana*
Varietal Denomination: Cannon-Sharp

(75) Inventor: Adam H. Cannon, Brooksville, FL (US)

(73) Assignee: STF CT JV LLC, Lutz, FL (US)

( * ) Notice: Subject to any disclaimer, the term of this patent is extended or adjusted under 35 U.S.C. 154(b) by 0 days.

(21) Appl. No.: 11/889,537

(22) Filed: Aug. 14, 2007

(51) Int. Cl.
*A01H 5/00* (2006.01)

(52) U.S. Cl. ..... Plt./225

(58) Field of Classification Search ..... Plt./225
See application file for complete search history.

*Primary Examiner*—Kent L Bell
(74) *Attorney, Agent, or Firm*—Buchanan Ingersoll & Rooney PC

(57) ABSTRACT

A distinctive Southern Live Oak tree is provided which was discovered as a chance seedling at Brooksville, Fla., U.S.A. The new variety is well-suited for growing as an easily-maintained quality shade tree in the landscape. The tree is a very rapid grower and displays a generally upright and substantially uniform and dense growth habit with a dominant central leader when mature. The lateral branches commonly are disposed at angles of greater than 60 degrees from the vertical in the substantial absence of included bark. Attractive dark green elongated and narrow leaves are formed which are glossy on the upper surface.

4 Drawing Sheets

Botanical/commercial classification: *Quercus virginiana*/ Southern Live Oak.
Varietal denomination: cv. Cannon-Sharp.

SUMMARY OF THE INVENTION

The new variety of *Quercus virginiana* was discovered at Brooksville, Fla., U.S.A., during 2003 while growing among a row of three-year-old common Southern Live Oak trees. The seed used to plant the row of trees had previously been collected from open-pollinated common Southern Live Oak trees growing at Madison, Fla., U.S.A. The new variety of the present invention is believed to be a chance seedling of unknown parentage. Had I not discovered and preserved the single tree of the new variety, it would have been lost to mankind.

I was primarily attracted to a single plant of the new variety in view of its rapid upright growth habit and its narrow glossy dark green leaves.

Upon further study and evaluation, it was confirmed that the new Southern Live Oak tree of the present invention possesses the following combination of characteristics:

(a) is rapidly growing and displays a generally upright and substantially uniform and dense growth habit with a dominant central leader when mature, (b) forms lateral branches that commonly are disposed at angles of greater than 60 degrees from the vertical, (c) forms attractive glossy dark green elongated and narrow leaves, and (d) is well suited for growing as an easily-maintained quality shade tree in the landscape.

The new variety is substantially free of included bark, holds its attractive generally uniform shape well, possesses a generally upright limb growth habit with an abundance of smaller limbs creating a dense canopy upon maturity, and has proven to be free form attack by fungi during observations to date. The new variety has been found to require little or no pruning once a caliper of 3 inches is reached.

The new variety can be grown to advantage in parks, gardens, and residential settings where an attractive and distinctive rapidly growing shade tree is desired.

The new variety can be readily distinguished from previously known *Quercus virginiana* plants. For instance, when compared to the 'SDLN' variety (U.S. Plant Pat. No. 12,015), the new variety is more rapidly growing, displays a more upright growth habit, and commonly forms narrower leaves which bear a glossy upper surface. When compared to the 'QVTIA' variety (U.S. Plant Pat. No. 11,219), the new variety also is more rapidly growing, displays a somewhat less upright growth habit and commonly forms narrower leaves which bear a glossy upper surface. Also, during observations to date the new variety commonly flushes approximately 10 days ahead of the 'SDLN' variety and approximately 28 days ahead of the 'QVTIA' variety. Both comparative varieties are commercially available in the southeastern portion of the United States, with the 'SDLN' variety being marketed under the CATHEDRAL OAK trademark and the 'QVTIA' variety being marketed under the HIGHRISE trademark.

Beginning in 2003 the new variety has been found to undergo asexual propagation at Groveland, Fla., U.S.A., by the rooting of softwood cuttings. Such asexual propagation has shown that the characteristics of the new variety are firmly fixed and are strictly transmissible form one generation to another. Accordingly, the new variety undergoes asexual propagation in a true-to-type manner.

The new variety has been named 'Cannon-Sharp.'

BRIEF DESCRIPTION OF THE PHOTOGRAPHY

The accompanying photographs show as nearly true as it is reasonably possible to make the same in color illustrations of this character, typical specimens and plant parts of the new variety. The plants of FIGS. 6 and 7 had been asexually reproduced through the use of softwood cuttings obtained from the originally discovered tree of FIGS. 1 and 2.

FIGS. 1 and 2 show during February, 2007, the originally discovered tree of the new variety at an age of approximately 6½ years while growing at Brooksville, Fla., U.S.A. Even though the photographs were obtained while the plant was dormant, the plant continues to exhibit an excellent foliage appearance. At the far left of FIGS. 1 and 2, the typical appearance of a common Southern Live Oak tree at this time of the year also is visible.

DETAILED DESCRIPTION

Figure 1:
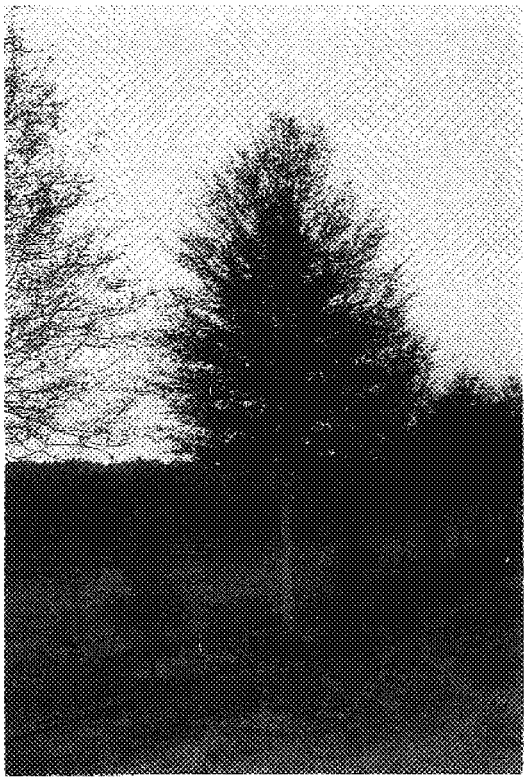
Figure 2:
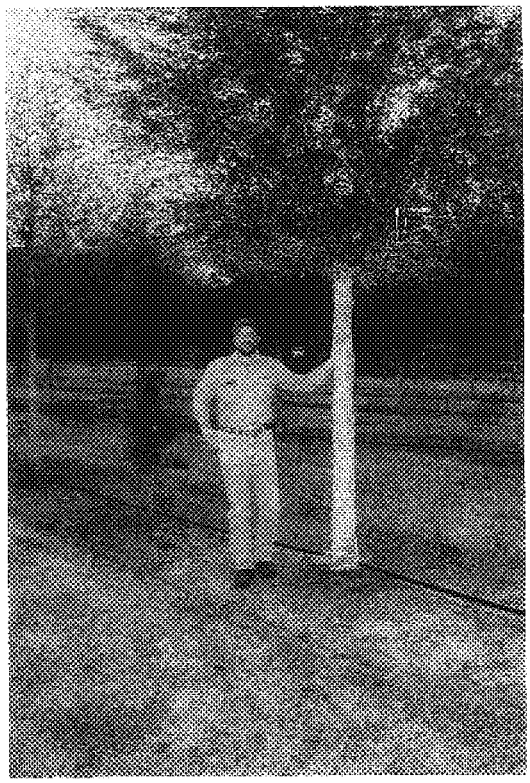
FIG. 2 shows a closer view of the rough bark of the new variety that commonly is displayed.
Figure 3:
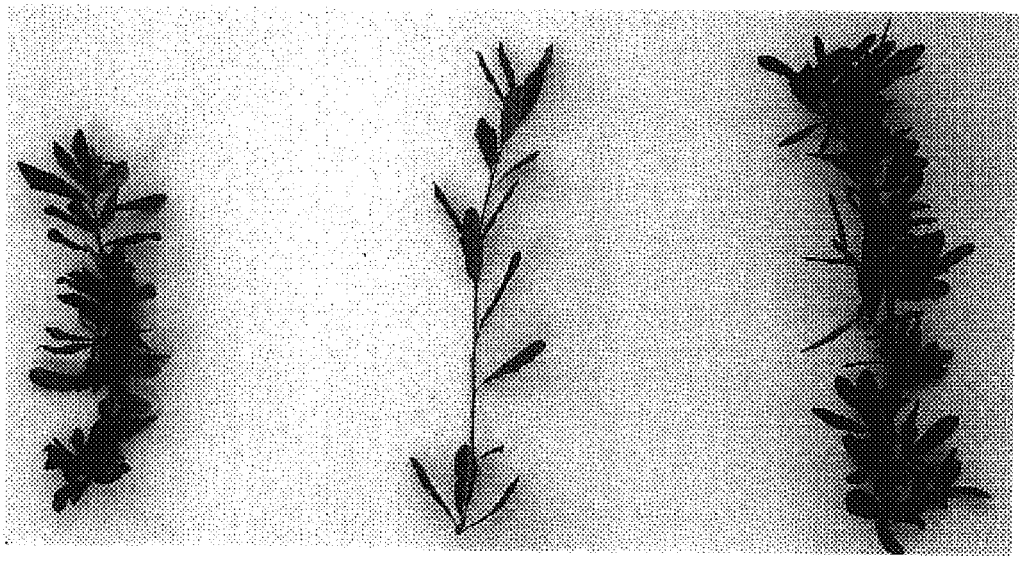
FIG. 3 shows for comparative purposes typical branches and foliage of the new variety (right), the 'SDLN' variety (left), and the 'QVTIA' variety (center). It is apparent that the narrow leaves of the new variety are more numerous and are more densely presented than the leaves of the 'QVTIA' variety.
Figure 4:
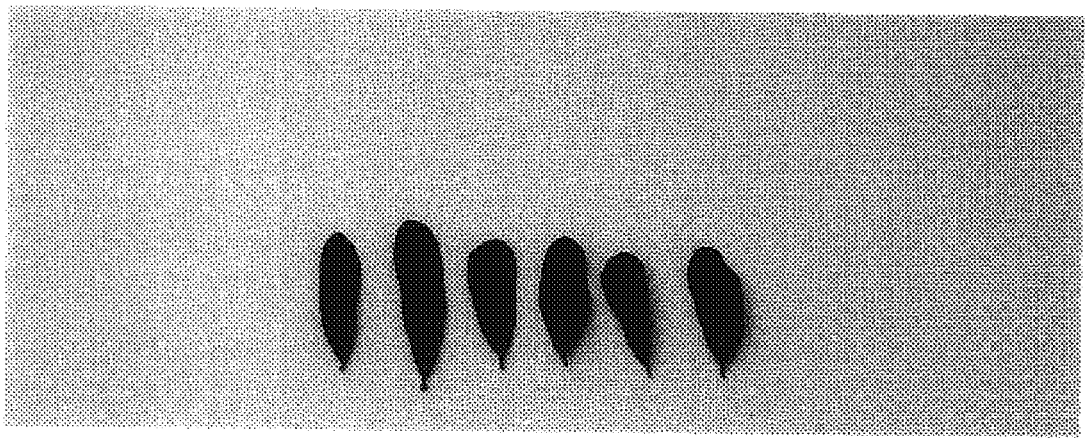
FIG. 4 shows the upper surfaces of typical leaves of the new variety.
Figure 5:
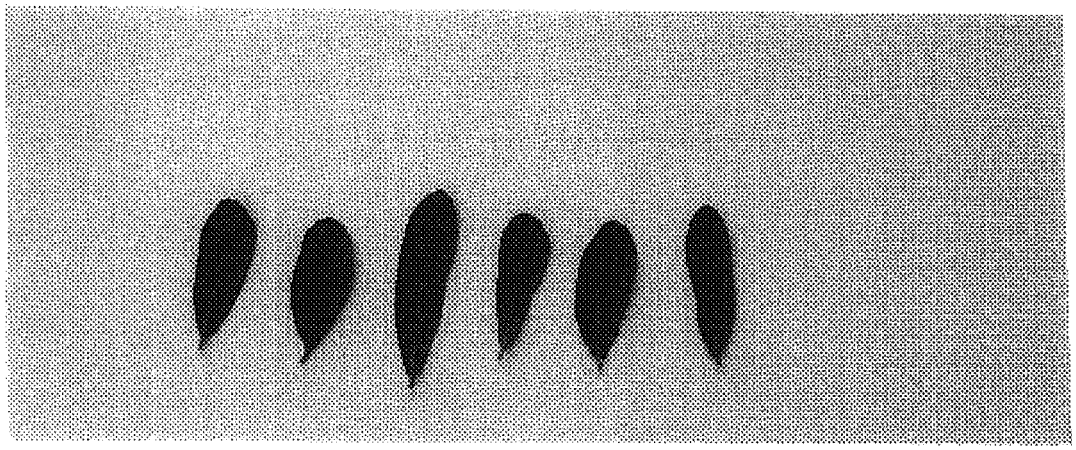
FIG. 5 shows the lower surfaces of typical leaves of the new variety.
Figure 6:
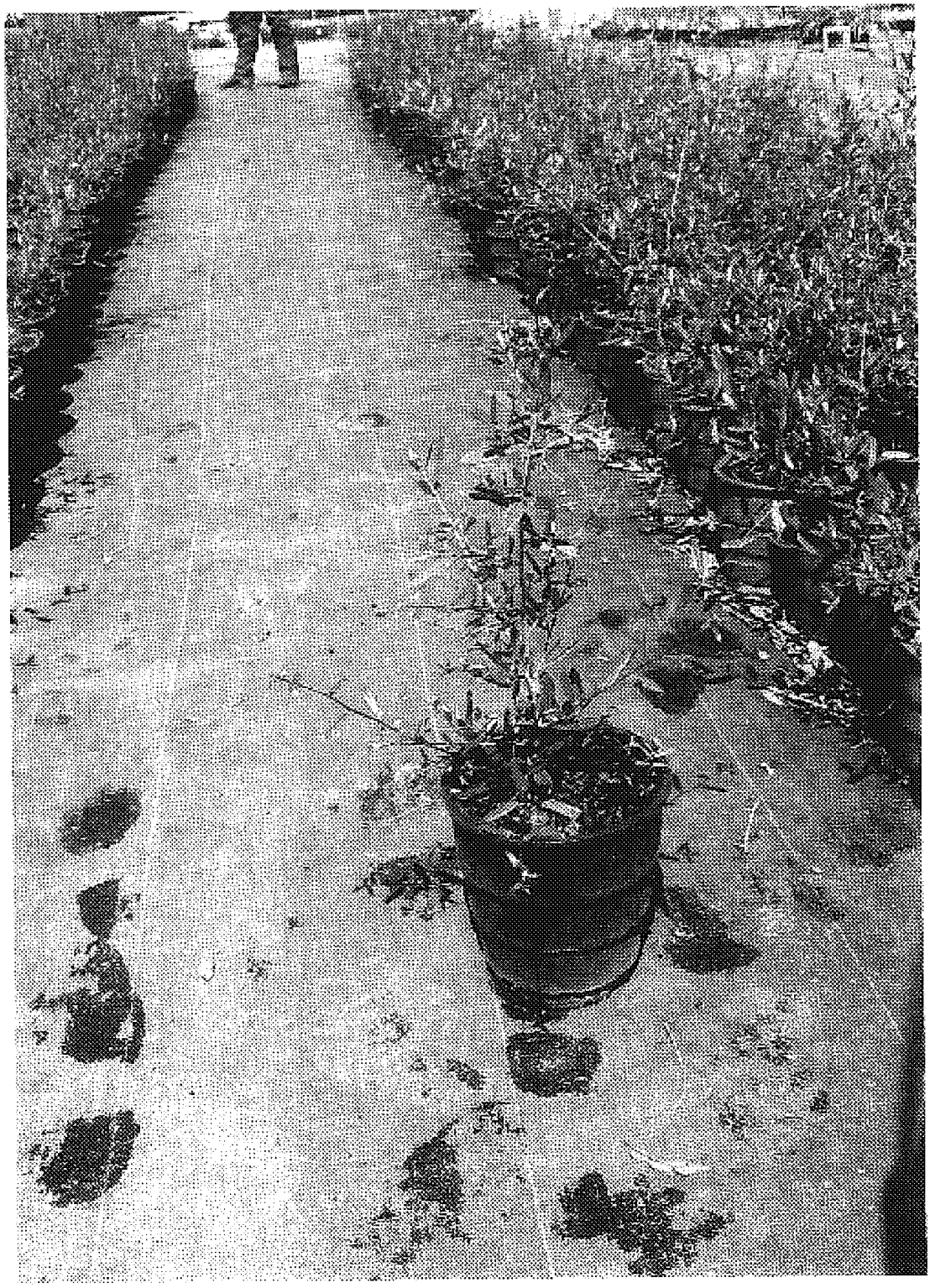
FIG. 6 shows the typical liner plants of the new variety at an age of approximately four months while being grown in one-gallon containers at Fruitland, Fla., U.S.A. The glossy upper leaf surfaces are apparent.
Figure 7:
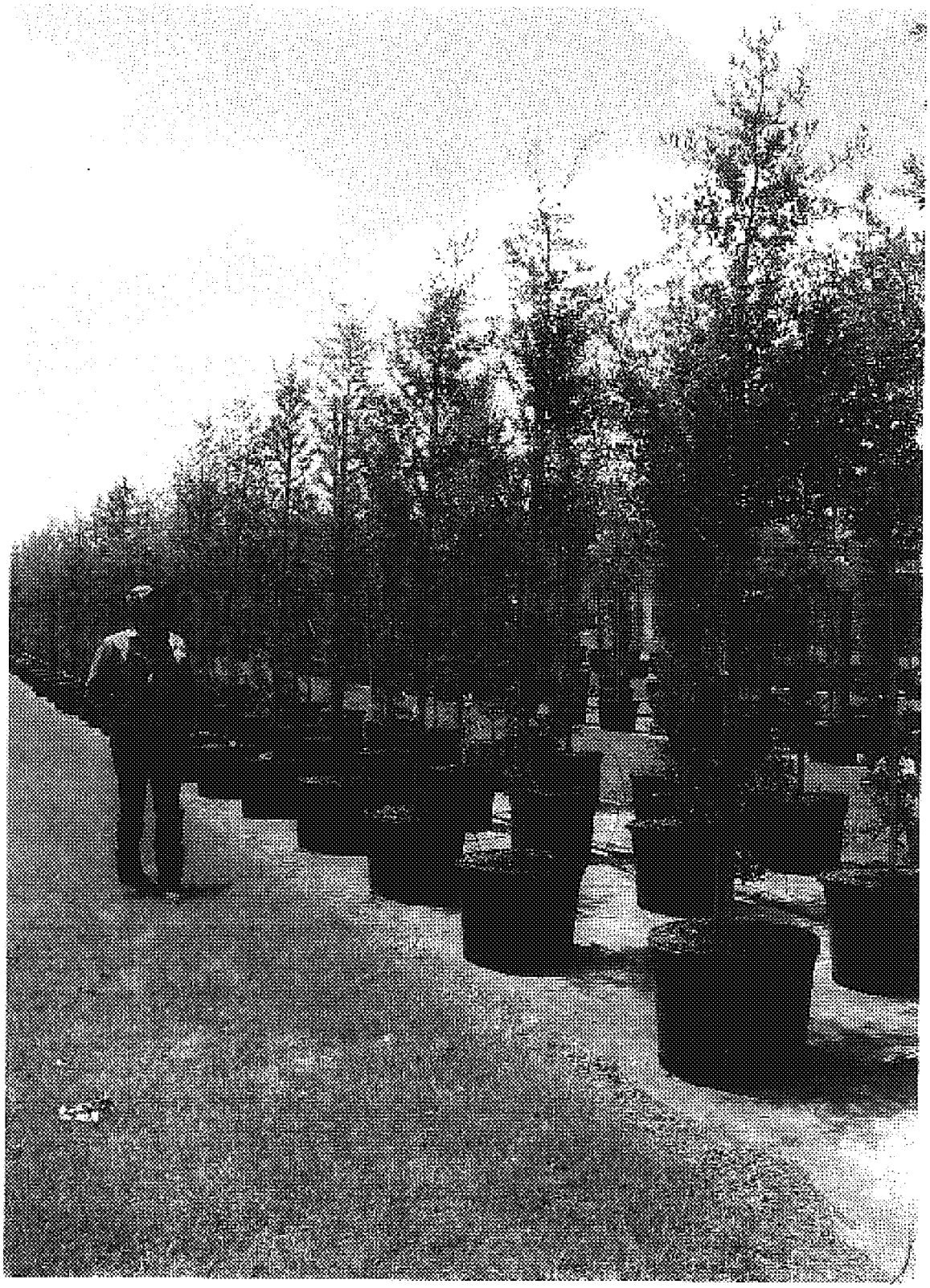
FIG. 7 shows typical trees of the new variety having an age of approximately 2½ years during May, 2007, while being grown in thirty-gallon containers at Webster, Fla., U.S.A. The rapid growth of the new variety is apparent.

The chart used in the identification of the colors is that of the Royal Horticultural Society (R.H.S. Colour Chart) of London, England. Color terminology in common terms sometimes is used. Such color terminology is to be accorded its customary dictionary significance. The description is based on the observation of plants of the new variety being grown at Brooksville, Fla. U.S.A., and at Webster, Fla., U.S.A.

Plant:

*Parentage.*—Chance seedling of *Qercus virginiana* of unknown parentage growing in a cultivated area at Brooksville, Fla., U.S.A.

*Type.*—Evergreen when grown in the southeastern portion of the United States. Under such growing conditions the foliage remains attractive even when dormant.

*Tree shape.*—Generally upright and uniform growth habit with a pronounced dominant central leader which commonly is lacking in traditional Southern Live Oak trees. The growth habit is more upright than that of the 'SDLN' variety (U.S. Plant Pat. No. 12,015) and somewhat less upright than that of the 'QVTIA' variety (U.S. Plant Pat. No. 11,219). The generally upright growth habit renders the new variety to be well suited for growing at sites where a wider tree breadth is undesirable.

*Branch angle.*—Lateral branches commonly display angles of greater than 60 degrees from the vertical thereby substantially eliminating the presence of undesirable included bark. This can be compared to branch angles of approximately 50 to 60 degrees which commonly are displayed by the 'QVTIA' variety.

*New growth.*—Commonly flushes approximately 10 days prior to the 'SDLN' variety and approximately 28 days prior to the 'QVTIA' variety during observation to date under the same growing conditions.

*Leaves.*—Relatively small and narrow, variable in size, commonly approximately 1 to 1½ inches in length, commonly approximately ¼ to ½ inch in width at the widest point, densely positioned on branches, emerging leaves commonly are near Greyed-Purple Group 184C in coloration, young summer leaves are commonly near Green Group 139A on the upper surface and near Yellow-Green Group 147C on the under surface, and mature leaves are commonly dark green, near Green Group 131A, on the upper surface and near Yellow-Green Group 147C on the under surface.

*Tree canopy.*—Relatively dense and attractive when mature. This can be compared to the generally open and non-uniform appearance of traditional Southern Live Oak trees.

Inflorescence:

*Time.*—Flowers at substantially the same time as the 'SDLN' and 'QVTIA' varieties.

*Type.*—Monoecious as traditional Southern Live Oak trees.

*Fertility*—Has not been evaluated to date.

*Acorns.*—Are beginning to form on the originally discovered tree, and in the absence of maturity have not been evaluated to date.

Development:

*Vigor.*—Very vigorous with rapid growth. During May 2007, the originally discovered tree was approximately 6½ years of age and had a caliper of approximately 6½ inches. At this age, under the same growing conditions, a typical tree of the 'SDLN' variety has a caliper of approximately 6 inches or less, a typical tree of the 'QVTIA' variety has a caliper of approximately 5 inches, and a traditional Southern Live Oak seedling has a caliper of approximately 4 to 5½ inches. During May 2007, the originally discovered tree has achieved a height of approximately 25 to 26 feet. This can be compared to a height of approximately 18 to 20 feet for a tree of the 'QVTIA' variety of the same age when grown at the same location.

*Heat resistance.*—Performs well during observations to date even when temperatures exceed 100° F.

*Cold resistance.*—has well withstood winter temperatures of 15 to 20° F.

*Resistance to fungi.*—Good.

*Resistance to pests.*—performs well while using conventional insecticide culture conditions.

*Usage.*—Distinctive rapidly-growing quality shade tree for use in parks, gardens, and residential settings.

I claim:

1. A new and distinct Southern Live Oak tree having the following combination of characteristics:

(a) is rapidly growing and displays a generally upright and substantially uniform and dense growth habit with a dominant central leader when mature, (b) forms lateral branches that commonly are disposed at angles of greater than 60 degrees from the vertical, (c) forms attractive glossy dark green elongated and narrow leaves, and (d) is well suited for growing as an easily-maintained quality shade tree in the landscape;

substantially as illustrated and described.

* * * * *